(12) United States Patent
Fatone et al.

(10) Patent No.: US 11,259,852 B2
(45) Date of Patent: Mar. 1, 2022

(54) PLATE CONNECTION

(71) Applicant: DEPUY SYNTHES PRODUCTS, INC., Raynham, MA (US)

(72) Inventors: Peter Fatone, West Chester, PA (US); Stefan Dudé, Neuendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 125 days.

(21) Appl. No.: 16/553,676

(22) Filed: Aug. 28, 2019

(65) Prior Publication Data

US 2021/0059727 A1 Mar. 4, 2021

(51) Int. Cl.
*A61B 17/80* (2006.01)
*A61B 17/17* (2006.01)
*A61B 17/74* (2006.01)
*A61B 17/00* (2006.01)

(52) U.S. Cl.
CPC ...... *A61B 17/8061* (2013.01); *A61B 17/1728* (2013.01); *A61B 17/8047* (2013.01); *A61B 17/742* (2013.01); *A61B 17/8023* (2013.01); *A61B 17/8057* (2013.01); *A61B 2017/00477* (2013.01)

(58) Field of Classification Search
CPC ............ A61B 17/8023; A61B 17/8004; A61B 17/8061; A61B 17/8052; A61B 17/1728; A61B 17/8047; A61B 17/8057; A61B 17/80; A61B 17/74; A61B 17/742; A61B 2017/00477

USPC ................................ 606/71, 280, 69–70, 73
See application file for complete search history.

(56) References Cited

U.S. PATENT DOCUMENTS

| | | | |
|---|---|---|---|
| 5,484,439 A | 1/1996 | Olson et al. | |
| 7,335,204 B2* | 2/2008 | Tornier | A61B 17/8061 606/280 |
| 8,579,898 B2* | 11/2013 | Prandi | A61B 17/80 606/71 |
| 9,956,015 B2* | 5/2018 | Ehmke | A61B 17/8023 |
| 2007/0055253 A1 | 3/2007 | Orbay et al. | |
| 2013/0090656 A1 | 4/2013 | Huebner et al. | |

* cited by examiner

*Primary Examiner* — Marcela I. Shirsat
(74) *Attorney, Agent, or Firm* — Fay Kaplun & Marcin, LLP

(57) ABSTRACT

A bone fixation system includes a first plate including a plate body and a connection portion extending distally therefrom, the connection portion including a positioning tab at a distal end thereof, the connection portion including a first opening extending therethrough and a ramped part, and a second plate including a coupling aperture along a proximal portion thereof, the coupling aperture configured to receive the positioning tab therein, the coupling aperture including a ramped proximal face configured to abut against the ramped part of the second surface of the positioning tab when the positioning tab is inserted into the coupling aperture, the head portion including a second opening extending therethrough. A connection screw configured to extend through the first opening and the second opening to couple the first and second plates together. Tightening the screw translates the ramped proximal face along the ramped part, eliminating a connection gap therebetween.

20 Claims, 3 Drawing Sheets

PLATE CONNECTION

FIELD

The invention relates to bone plates to be used for the treatment of bones.

BACKGROUND

Fractures such as periprosthetic fractures around implants are often treated using a modular bone plate system including multiple bone plates. Theses bone plate systems allow screws to be inserted into cancellous bone without interfering with an intramedullary canal that may contain a nail or stem of a prosthesis. In some cases, it is necessary to combine or connect two separate bone plates. However, often times when two bone plates are connected, clinical loads are realized within the coupling between the two plates. For example, torsional and shear loads, when applied to the bone plates, may be transmitted to the coupling therebetween, deforming the coupling. More robust coupling designs between two bone plates often require multiple connecting screws or fixation elements to shield the coupling from these clinical loads. However, couplings that require multiple screws are more difficult to install and require a first person to hold the bone plates together while a second person tightens the screws.

SUMMARY

The present disclosure relates to a bone fixation system, comprising a first plate including a plate body extending from a proximal end to a distal end and including a plurality of bone fixation openings extending therethrough from a first surface of the body which, when the bone plate is in an operative position, faces away from the bone, to a second surface which, when the bone plate is in an operative position, faces the bone. The first plate further includes a connection portion extending distally from the plate body, the connection portion including a positioning tab at a distal end thereof, the connection portion including a first opening extending from the first surface to the second surface, the second surface of the connection portion including a ramped part. A second plate extends from a proximal end to a distal end and includes a coupling aperture along a proximal portion thereof, the coupling aperture configured to receive the positioning tab therein, the coupling aperture including a ramped proximal face configured to abut against the ramped part of the second surface of the positioning tab when the positioning tab is inserted into the coupling aperture. The head portion including a second opening extending therethrough from a first surface of the second plate which, when the second plate is in an operative position, faces away from the bone, to a second surface which, when the bone plate is in an operative position, faces toward the bone. A connection screw is configured to extend through the first opening and the second opening to couple the first and second plates together, wherein tightening the connection screw translates the ramped proximal face along the ramped part, eliminating a connection gap therebetween.

The present disclosure also relates to a bone fixation system, comprising a base plate defined via a first surface which, in an operative position, faces away from the bone, and a second surface which, in the operative position, faces toward the bone, and including a head portion and a shaft portion extending distally from the head portion, the head portion including an engagement portion extending along the first surface of the head portion, the engagement portion including a coupling aperture at a distal end thereof, a ramped face tapering toward the coupling, and an attachment plate defined via a first surface which, in an operative position, faces away from the bone, and a second surface which, in the operative position, faces toward the bone, and including a plate body and a connection portion extending distally therefrom for coupling the attachment plate to the base plate, the connection portion sized and shaped to engage the engagement portion of the base plate and including a positioning tab at a distal end thereof, the positioning tab sized and shaped to be inserted through the coupling aperture so that the positioning tab is engageable with a portion of the second surface of the base plate distal of the coupling aperture, the connection portion including a ramped portion extending along the second surface thereof so that, when the positioning tab is inserted into the coupling aperture, the ramped portion is slidable along the ramped face to eliminate a connection gap between the connection portion and the engagement portion.

BRIEF DESCRIPTION

DETAILED DESCRIPTION

Figure 1:
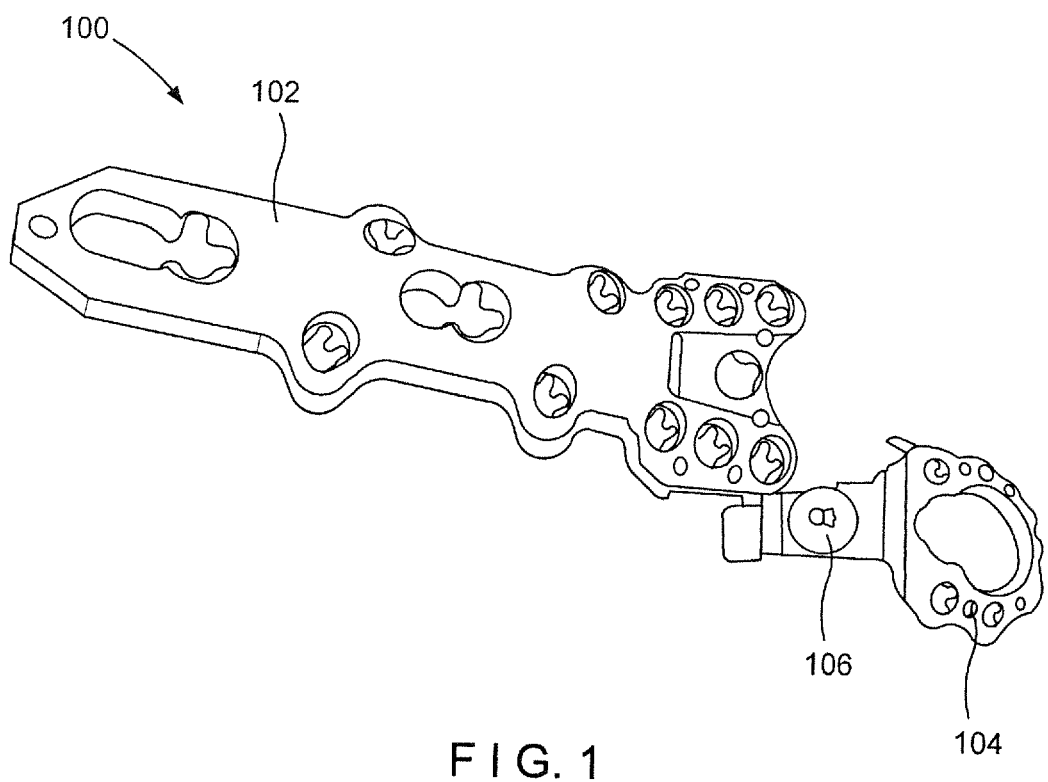
FIG. 1 shows a top view of a bone fixation system according to an exemplary embodiment of the present disclosure.

The present disclosure may be further understood with reference to the following description and the appended drawings, wherein like elements are referred to with the same reference numerals. The present embodiments relate to the treatment of a bone and, in particular, relates the treatment of periprosthetic fractures. Exemplary embodiments describe a bone fixation system comprising a first bone plate and a second bone plate configured to be coupled to one another via a tabbed connection. The tabbed connection includes a mating feature which promotes self-alignment of one of the bone plates relative to the other prior to fastening the two bone plates together. The design of this mating feature eliminates gaps between the two plates on areas that require resistance to clinical loads. This mating feature also enables a single screw connection between the two plates and resists clinical loads without the screw installed. In one exemplary embodiment, as described below, the first bone plate and the second bone plate of the bone fixation system may include a base plate and an attachment plate specifically configured for treatment of a femur. It will be understood by those of skill in the art, however, that the mating features described below may be used to attach any two bone plates for the fixation of any of a variety of bones. It should be noted that the terms "proximal" and "distal," as used herein, are intended to refer to a direction toward (proximal) and away from (distal) a mass of the human body.

Figure 2:
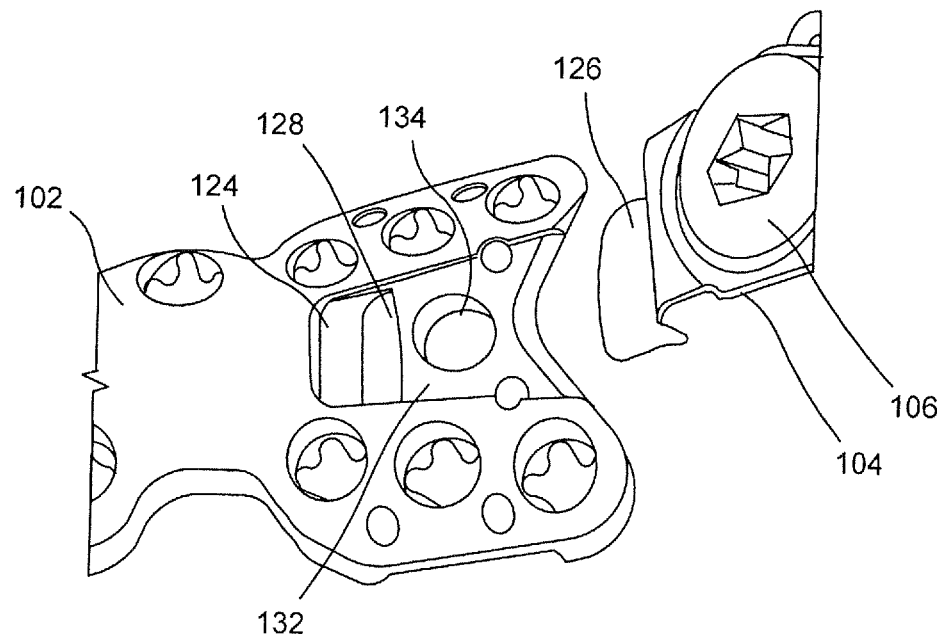
FIG. 2, shows a perspective view of the bone fixation system of FIG. 1.
Figure 3:
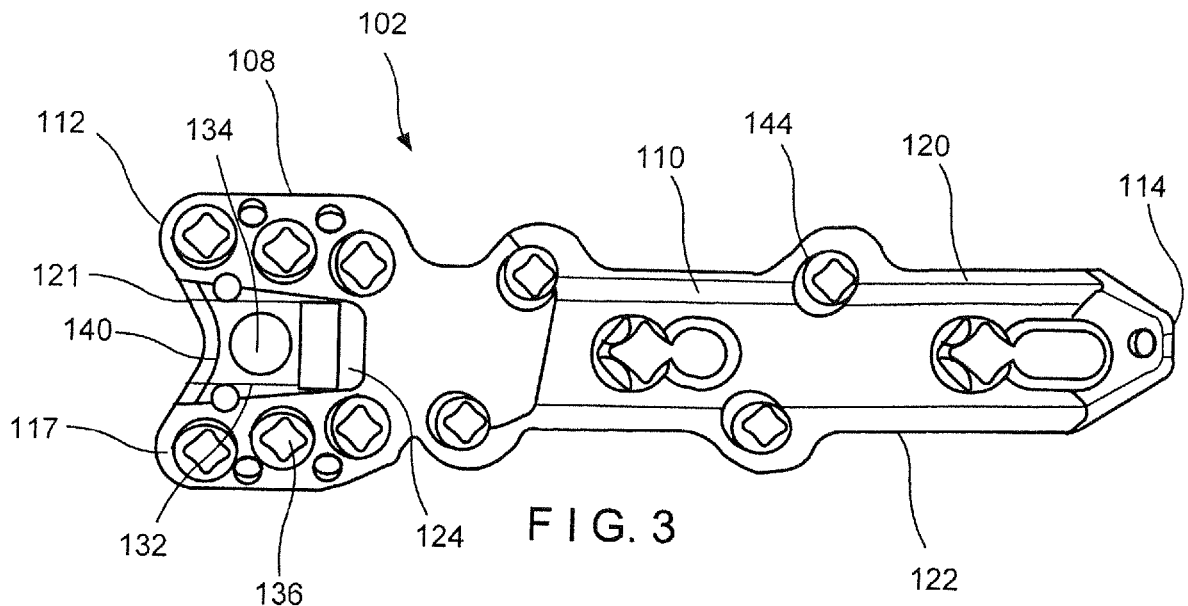
FIG. 3 shows a top plan view of a base plate of the bone fixation system of FIG. 1.

As shown in FIGS. 1-2 a bone fixation system 100 according to an exemplary embodiment of the present disclosure comprises a base plate 102 and an attachment plate such as, for example, a ring plate 104, along with a connection screw 106. Although the exemplary embodiments show and describe the attachment plate as a ring plate 104, it will be understood by those of skill in the art that the bone fixation system 100 may include any of a variety of attachment plates configured to treat any of a variety of bones. Turning to FIGS. 2-3, the base plate 102 generally comprises a head portion 108 and a shaft portion 110 configured to be mounted over portion of a long bone such as, for example, a femur. In an exemplary embodiment, the base plate 102 is implanted in a target position with the shaft portion 110 extending over, for example, a shaft of the femur with the head portion 108 positioned over a vastus ridge of the femur.

The base plate 102 extends along a longitudinal axis from a proximal end 112 to a distal end 114 and is defined via a first surface 116 which, when the base plate 102 is in an operative position along a bone, faces away from a lateral aspect of the femur, and a second surface 118 which, when the base plate 102 is in the operative position, faces the bone. The base plate 102 may be any preferred length such as, for example, between 118-388 mm. However, it will be understood that this range is only exemplary. Longitudinal sides 120, 122 extend longitudinally between the first and second surfaces 116, 118 from the proximal end 112 to the distal end 114. The second surface 118, in an exemplary embodiment, is contoured to match the contour of a target portion of a surface of the portion of bone over which it is to be positioned. For example, in this embodiment, the second surface 118 is contoured to generally match the shape of the portion of the femur over which it is to be mounted. The base plate 102 also includes a proximal face 117 connecting the first surface 116 to the second surface 118 between the two longitudinal sides 120, 122, at the proximal end 112. The proximal face 117 is configured to interface with a bone-facing surface of the ring plate 104, as will be described in further detail below. The head portion 108, in this embodiment, has a width (i.e., a distance between the longitudinal sides 120, 122) greater than a width of the shaft portion 110. However, it will be understood that the head and shaft portions 108, 110 may have any dimension depending on the procedure to be performed or the bone surface on which the base plate 102 is to be implanted and, for example, any implant that has previously been inserted into the bone.

Figure 5:
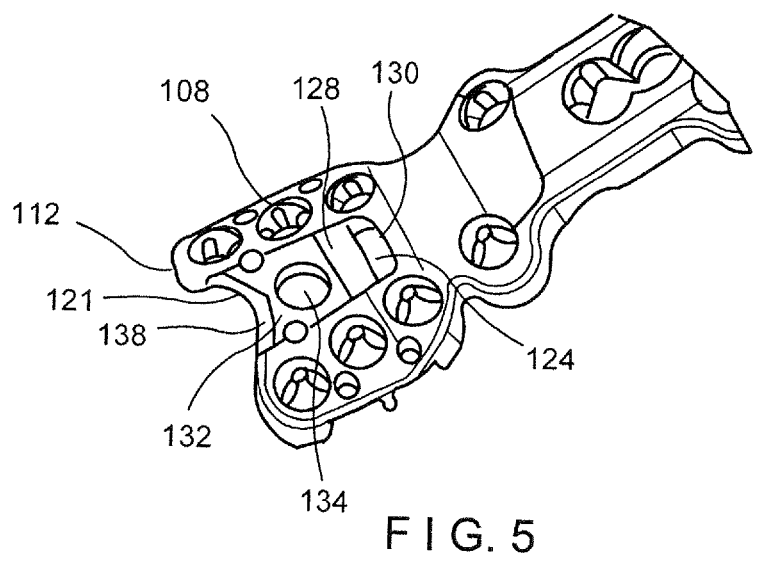
FIG. 5 shows a perspective view of a proximal portion of the base plate of the bone fixation system of FIG. 1.

The head portion 108 includes a coupling aperture 124 at a distal portion thereof configured to receive a positioning tab 126 of the ring plate 104. The aperture 124, as shown in FIG. 2, extends from the first surface 116 to the second surface 118 and includes a ramped proximal face 128 and a distal face 130. The coupling aperture 124, in this embodiment, is in communication with a longitudinal grooved or indented bone plate engagement portion 132 extending to the proximal end 112 of the plate and configured to receive a proximal connecting portion 160 of the ring plate 104. As can be seen in FIGS. 2 and 5, the ramped proximal face 128 of the coupling aperture 124 extends from the second surface 118 to the indented portion 132. The ramped proximal face 128, in this embodiment, has an angle α, the angle α being for example, between 20 and 40 degrees and, more particularly, approximately 30 degrees relative to the second surface 118.

However, it will be understood that the proximal face 128 may be angled at any preferred degree depending on the application or procedure in which the system 100 is used. The indented bone plate portion 132 includes a central opening 134 extending through the base plate 102 to the second surface 118 sized and shaped to receive the connection screw 106. The central opening 134, in this embodiment, includes an internal threading on an inner surface thereof configured to mate with an external threading on the outer surface of the connection screw 106. Although the central opening 134, in this embodiment, is shown and described as extending through a central portion of the indented plate portion 132, it will be understood by those of skill in the art that the central opening 134 may extend through any portion of the indented plate portion 132 so long as the central opening 134 is configured to receive the connecting screw 106 therein. The head portion 108 also includes a plurality of bone fixation openings 136 extending therethrough from the first surface 116 to the second surface 118. In the embodiment of FIG. 1, the head portion 108 includes six bone fixation openings 136. However, it will be understood that the head portion 108 may have any number of bone fixation openings in any desired configuration, depending on the procedure in which the bone fixation system 100 is being used.

Figure 8:
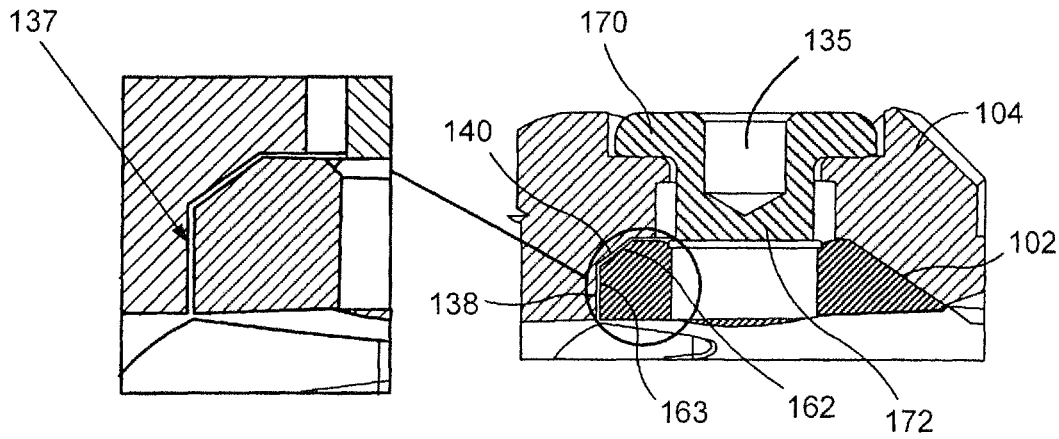
FIG. 8 shows a side cross-sectional view of the coupling between the base plate and the ring plate of the bone fixation system of FIG. 1.

A medial portion 121 (between the two longitudinal sides) of the proximal face 117 of the head portion 108, as noted above, is configured to interface with a bone-facing second surface 152 of the ring plate 104. That is, when the ring plate 104 is positioned with the positioning tab 126 within the coupling aperture 124, the medial portion 121 of the proximal face 117 abuts a wall or ledge on the bone-facing second surface 152 of the ring plate 104 that has a shape or profile corresponding to a profile of the medial portion 121, as will be described in further detail below. In an exemplary embodiment shown in FIGS. 3-5, the medial portion 121 includes a first part 138 extending perpendicularly relative to the second surface 118 and a second part 140 extending at a non-perpendicular angle from the first part 138 to the first surface 116, as best seen in FIG. 8. The second part 140 may be angled at approximately 110-130 degrees relative to the first surface 116.

Figure 4:
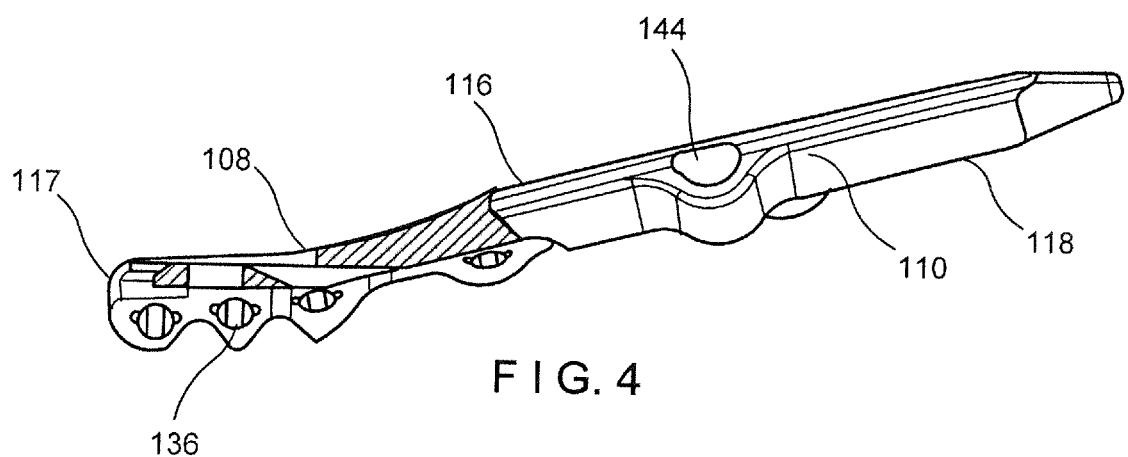
FIG. 4 shows a side view of the base plate of the bone fixation system of FIG. 1.

The shaft portion 110 of the base plate 102, in this embodiment, includes a plurality of bone fixation openings 144 extending therethrough from the first surface 116 to the second surface 118, as shown in FIGS. 3-4. It will be understood by those of skill in the art, however, that the number of bone fixation element openings 144 shown in the present embodiment is exemplary only and that the shaft portion 110 may have any number of bone fixation openings 144 extending therethrough in any of a variety of spacings and configurations. For example, in some embodiments, the bone fixation openings 144 may be aligned along the longitudinal axis of the base plate 102 or may be staggered relative to the longitudinal axis of the base plate 102. In this embodiment, the bone fixation openings 144 are variable angle locking holes through which a bone fixation element such as, for example, a variable angle locking screw, may be inserted at any user selected angle (within a supported range of angulation) relative to central axes thereof as would be understood by those skilled in the art. Thus, the angle of the locking screws can be chosen by the physician depending on the patient's anatomy and the location of the base plate 102 relative to a fracture.

Figure 6:
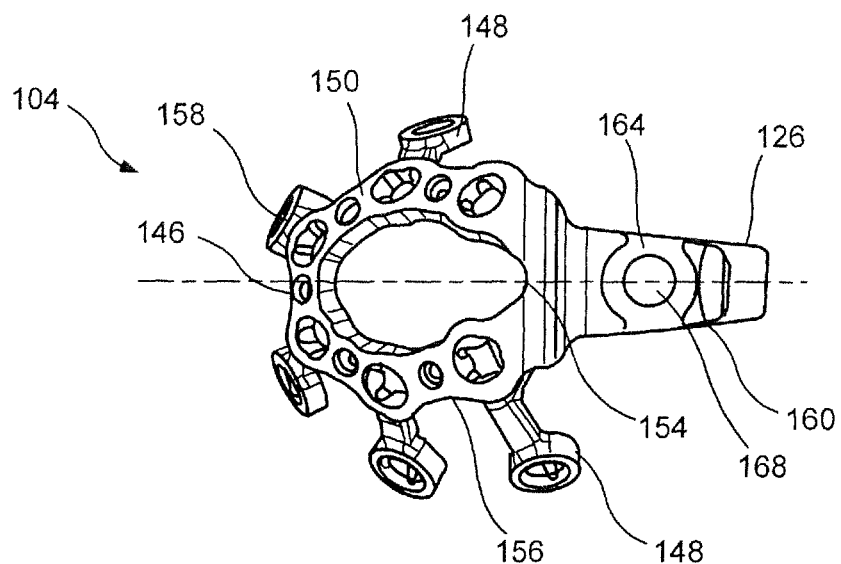
FIG. 6 shows a top plan view of a ring plate of the bone fixation system of FIG. 1.
Figure 7:
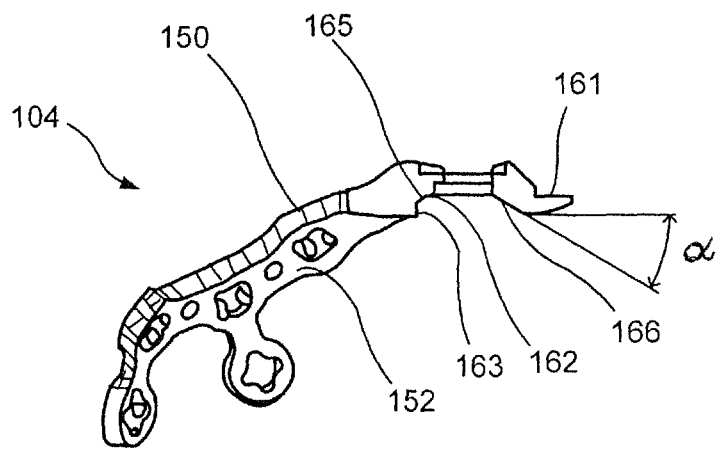
FIG. 7 shows a side view of the ring plate of the bone fixation system of FIG. 1.

The ring plate 104, as shown in FIGS. 6-7, is a plate including a substantially circular central body 146 with, in this embodiment, five projections 148 extending radially outward from the central body 146. However, it will be understood that while the current embodiment includes five projections, any number of projections may be used. The central body 146 may be shaped as a ring defined via a first surface 150 which, when the ring plate 104 is in an operative position along a bone, faces away from the bone, a second surface 152 which, when the ring plate 104 is in the operative position, faces the bone, and substantially annular inner and outer surfaces 154, 156 extending therebetween. The second surface 152, in an exemplary embodiment, is contoured to correspond to an external surface of the portion of bone on which it is to be positioned. For example, in this embodiment, the second surface 152 is contoured to generally match the shape of the portion of the femur on which it is to be mounted.

The central body 146 may include bone fixation openings 158 positioned thereabout between the annular inner and outer surfaces 154, 156. The bone fixation openings 158 extend through the ring plate 104 from the first surface 150 to the second surface 152. Each projection 148 also includes a bone fixation opening 158 at a radial tip thereof. In this embodiment, the bone fixation openings 158 are variable angle locking holes through which a bone fixation element such as, for example, a variable angle locking screw, may be inserted at any user selected angle (within a supported range of angulation) relative to central axes thereof. However, it will be understood that the bone fixation openings 158 may be any preferred type of opening.

The ring plate 104 includes a distal connecting portion 160 extending distally from the central body 146 and configured to be seated in the engagement portion 132 of the base plate 102. The connecting portion 160 includes the positioning tab 126 at a distal end thereof which, as noted above, is configured to be received within the coupling aperture 124 of the base plate 102. The geometry of the positioning tab 126 conforms to the geometry of the coupling aperture 124 with a flat surface 161 extending parallel to a longitudinal plane of the connecting portion 160 and is configured to be received distally through the coupling aperture 124 to be positioned substantially adjacent to the second surface 118 of the base plate 102. The second surface 152 of the connection portion 160 has a geometry that conforms with the first surface 116 of the engagement portion 132 of the base plate 102. For example, as best illustrated in FIG. 7, a proximal part 162 of the second surface 152 of the connection portion 160 includes the wall 163 formed to mate with the medial portion 121 of the proximal face 117 of the base plate 102. In an exemplary embodiment, the wall 163 includes an angled portion 165 that is slanted at the same angle as the second portion 140 of the medial portion 121 of the proximal face 117 so that any connection gap occurring between the base plate 102 and the ring plate 104 is minimized/eliminated.

A medial part 164 of the connecting portion 160, which is distal to the proximal part 162, is sized, shaped and configured to fit over a correspondingly sized, shaped and configured engagement portion 132 of the base plate 102. The connecting portion 160 has a width (a dimension between two longitudinal sides of the connecting portion 160) that matches the width of the engagement portion 132 of the base plate 102 so that the ring plate 104 can be easily fitted over the base plate 102 in the correct orientation. Similarly, a distal part 166 of the connecting portion 160, extending toward the positioning tab 126, has a second surface geometry that conforms to the geometry of the proximal face 128 of the coupling aperture 124. Specifically, the distal part 166 is ramped at the same angle α as the proximal face 128 (i.e., approximately 30 degrees relative to the longitudinal axis of the connecting portion 160), as shown in FIG. 5. Again, this matching geometry provides a close fit between the base plate 102 and the ring plate 104 when the two plates are coupled together.

As can be seen in FIG. 6, the connecting portion 160 includes a central hole 168 extending therethrough from the first surface 150 to the second surface 152, the central hole 168 being sized and shaped to receive the connection screw 106. Although the central hole 168 is shown and described as extending through a central portion of the connection portion 160, it will be understood by those of skill in the art that the central hole 168 may extend through any portion of the connecting portion 160 so long as the central hole 168 is configured to receive a portion of the connecting screw 106 therethrough, when the base plate 102 and the ring plate 104 are coupled to one another as described below. To couple the base plate 102 and the ring plate 104 together, the central hole 168 may be positioned over the central opening 134 of the base plate 102. The central hole 168 and the central opening 134 are not required to be axially aligned. Rather, the central hole 168 "floats" over the central opening 134 so that the central hole 168 may be shifted over the central opening 134.

In one embodiment, the central hole 168 may have a slightly larger diameter than the central opening 134 to facilitating shifting of the central hole 168 over the central opening 134 as the ramped distal part 166 slides along the ramped proximal face 128 when the base plate 102 and the ring plate 104 are coupled together, as will be described in further detail below. In this embodiment, a central axis of the central hole 168 and a central axis of the central opening 134 may be coplanar, the central axes of the central hole 168 and the central opening 134 extending along a plane, for example, that extends substantially perpendicular to the first surfaces 116, 150 and/or the second surfaces 118, 152 of the base plate 102 and the ring plate 104, respectively, and through longitudinal axes of the base and ring plates 102, 104. The central hole 168, in this embodiment, may have a smooth inner surface which acts as a through-hole through which the connection screw 106 extends. It will be understood by those of skill in the art, however, that the central hole 168, in another embodiment, may have an internal threading along an inner surface thereof for mating with an external threading on an outer surface of the connection screw 106.

The connection screw 106, as one skilled in the art would understand, may be any regular screw including a head portion 170 and a shaft portion 172, as depicted in FIG. 8. The shaft portion 172, in this embodiment, includes threading along an outer surface thereof configured to mate with a threading on the inner surfaces of the central opening 134 and/or the central hole 168. The head portion 170 may be large enough to be grasped by the physician for initial manual tightening of the connection screw 106. However, the head portion 170 may include a driver receiving portion 135 so as to be engaged by a driver for final tightening of the connection screw 106. It is noted, however, that the connection between the base plate 102 and the ring plate 104 is configured such that the bone plates 102, 104 still resist clinical loads even prior to insertion of the connection screw 106 therein.

As would be understood by those skilled in the art, the matching geometries of the connecting portion 160 and positioning tab 126 of the ring plate 104 and the engagement portion 132 and coupling aperture 124 of the base plate 102 are configured to maximize the amount of surface area that is contact between the two plates. Thus, once the connection screw 106 is inserted into the bone plate system 100 and tightened, any gaps between the two plates 102, 104 are eliminated by the fit of the ramped proximal face 128 with the ramped distal part 166 of the connection portion 160 such that any torsional or sheer loads that the bone plates bear is not seen by the screw or the connection between the plates 102, 104 but rather, is born along the lengths of the plates themselves. Furthermore, the tongue and groove connection of the positioning tab 126 within the coupling aperture 124 allows the bone plates 102, 104 to be easily self-aligned such that only a single connection screw 106 is needed to keep the plates 102, 104 from rotating relative to one another.

According to an exemplary method of assembling the plates 102, 104, the positioning tab 126 of the ring plate 104 is inserted into the coupling aperture 124 of the base plate 102 from a non-bone-facing side of the base plate 102 at an oblique angle, as best shown in FIG. 2. In the course of inserting the positioning tab 126 into the coupling aperture 124, the ring plate 104 is rotated downwardly, or toward the plane of the base plate 102, by the self-aligning geometries of the positioning tab 126 and coupling aperture 124 until the ring plate 104 is seated over the base plate 102. When the ring plate 104 is seated over the base plate 102, the connection portion 160 is positioned within the engagement portion 132 and the positioning tab 126 is fully inserted through the coupling aperture 124 so that there is little to no space between the two plates 102, 104. At this point, as noted previously, the connection between the two plates 102, 104 is able to resist clinical loads without any screw connection therebetween. Furthermore, the connection between the positioning tab 126 and the coupling aperture 124 does not require the use of any screws or fasteners and can be made while the base plate 102 is mounted to a target bone, while the base plate 102 is detached from the target bone or while the base plate 102 is coupled with other bone plates.

Once the base plate 102 and the ring plate 104 have been mated together, the connection screw 106 is inserted first through the central hole 168 and then through the central opening 134. The connection screw 106 may be initially tightened by hand with final tightening completed using a driver. In another embodiment, the connection screw 106 may be tightened only using a driver. During final tightening of the connection screw 106 and the ring plate 104, the ramped proximal face 128 and the distal part 166 of the connection portion 160 force the ring plate 104 to translate along the ramp, eliminating any initial connection gap 137 that may have been present. As the ramped distal part 166 and the ramped proximal face 128 slide along one another to eliminate the connection gap, the shaft portion 172 of the connection screw 106 is coaxially aligned with the central axis of the central opening 134 of the base plate 102 and coplanar with the central hole 168 of the ring plate 104.

Although the exemplary embodiment shows and describes the system 100 as a femoral fixation system including the base plate 102 and the ring plate 104 connected to one another via a coupling mechanism including, in part, the coupling aperture 124 and the positioning tab 126, it will be understood by those of skill in the art the coupling mechanism of the present disclosure may be used to connect two plates for any of a variety of fixation systems.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A bone fixation system, comprising:
a first plate including a plate body extending from a proximal end to a distal end and including a plurality of bone fixation openings extending therethrough from a first surface of the body which, when the first plate is in an operative position, is configured to face away from a bone, to a second surface which, when the first plate is in an operative position, is configured to face the bone, the first plate further including a connection portion extending distally from the plate body, the connection portion including a positioning tab at a distal end thereof, the connection portion including a first opening extending from the first surface to the second surface, the second surface of the connection portion including a ramped part;
a second plate extending from a proximal end to a distal end and including a coupling aperture along a proximal portion thereof, the coupling aperture configured to receive the positioning tab therein, the coupling aperture including a ramped proximal face configured to abut against the ramped part of the second surface of the positioning tab when the positioning tab is inserted into the coupling aperture, the proximal end including a second opening extending therethrough from a first surface of the second plate which, when the second plate is in an operative position, is configured to face away from the bone, to a second surface which, when the first plate is in an operative position, is configured to face toward the bone; and
a connection screw configured to extend through the first opening and the second opening to couple the first and second plates together so that, as the connection screw is tightened, the ramped proximal face translates along the ramped part and one of the first and second openings shifts relative to the other of the first and second openings, eliminating a connection gap between the first and second plates.

2. The system of claim 1, wherein the second plate further includes an indented engagement portion on the first surface thereof, the engagement portion extending from the coupling aperture to the proximal end of the second plate, the engagement portion being sized and shaped to receive the connection portion of the first plate therein when the positioning tab is inserted into the coupling aperture.

3. The system of claim 2, wherein the second opening extends through the engagement portion.

4. The system of claim 1, wherein the first and second openings include threading on an interior surface thereof configured to mate with a threading on an outer surface of the connection screw.

5. The system of claim 1, wherein a portion of a proximal face of the second plate is configured to abut a correspondingly sized and shaped wall of the connection portion extending along the second surface of the first plate at a proximal end of the connection portion.

6. The system of claim 1, wherein the connection screw includes a shaft and a head configured to be manually tightened.

7. The system of claim 1 , wherein a first surface of the positioning tab is configured to abut a second surface of the proximal end, distal of the coupling aperture.

8. The system of claim 1, wherein the ramped proximal face is angled at 20 to 40 degrees relative to the second surface of the second plate.

9. The system of claim 8, wherein the angle of the ramped part relative to a second surface of the positioning tab corresponds to an angle of the ramped proximal face of the second plate.

10. The system of claim 1, wherein the positioning tab and the coupling aperture are configured to self-align to connect the first plate to the second plate.

11. The system of claim 1, wherein one of the first and second openings is larger than the other of the first and second openings.

12. A bone fixation system, comprising:
a base plate defined via a first surface which, in an operative position, is configured to face away from the bone, and a second surface which, in the operative position, is configured to face toward the bone, and including a head portion and a shaft portion extending distally from the head portion, the head portion including an engagement portion extending along the first surface of the head portion, the engagement portion including a coupling aperture at a distal end thereof, and a ramped face tapering toward the coupling aperture; and
an attachment plate defined via a first surface which, in an operative position, is configured to face away from the bone, and a second surface which, in the operative position, is configured to face toward the bone, and including a plate body and a connection portion extending distally there from for coupling the attachment plate to the base plate, the connection portion sized and shaped to engage the engagement portion of the base plate and including a positioning tab at a distal end thereof, the positioning tab sized and shaped to be inserted through the coupling aperture so that the positioning tab is engageable with a portion of the second surface of the base plate distal of the coupling aperture, the connection portion including a ramped portion extending along the second surface thereof so that, when the positioning tab is inserted into the coupling aperture, the ramped portion is slidable along the ramped face to eliminate a connection gap between the connection portion and the engagement portion, wherein the base plate includes a connection screw opening extending through a portion of the engagement portion proximal of the ramped face and the attachment plate includes a connection screw opening extending through a portion of the connection portion proximal of a ramped surface, the connection screw openings being configured so that, as a connection screw is tightened through the connection screw openings, the ramped portion slides along the ramped face and one of the connection screw openings shifts relative to the other of the connection screw openings to eliminate the connection gap.

13. The system of claim 12, wherein the connection screw opening of the base plate includes a threading configured to engage a correspondingly threaded exterior surface of a connection screw.

14. The system of claim 13, wherein, when the connection screw opening of the base plate is configured to receive a connection screw therein coaxially aligned with a central axis of the connection screw opening of the base plate.

15. The system of claim 12, wherein the base plate is configured in size and shape to extend along a portion of a length of a femur.

16. The system of claim 12, wherein the attachment plate is a ring plate and the plate body is substantially circular and configured to extend over proximal end of a femur.

17. The system of claim 16, wherein the ring plate includes a plurality of projections extending radially outward from the plate body, each of the projections including a bone fixation element receiving opening extending therethrough.

18. The system of claim 12, wherein the base plate includes a plurality of bone fixation element receiving openings extending therethrough.

19. The system of claim 12, wherein a proximal face of the engagement portion is configured to engage a correspondingly sized and shaped shoulder along the second surface of the connection portion, a gap between the proximal face of the engagement portion and the shoulder along the second surface of the connection portion decreasing as the ramped portion slides along the ramped face.

20. The system of claim 12, wherein one of the connection screw openings is larger than the other of the connection screw openings.

* * * * *

UNITED STATES PATENT AND TRADEMARK OFFICE
CERTIFICATE OF CORRECTION

| | | |
|---|---|---|
| PATENT NO. | : 11,259,852 B2 | Page 1 of 1 |
| APPLICATION NO. | : 16/553676 | |
| DATED | : March 1, 2022 | |
| INVENTOR(S) | : Fatone et al. | |

It is certified that error appears in the above-identified patent and that said Letters Patent is hereby corrected as shown below:

In the Claims

Claim 12, Column 9, Line 17:
"hone, and a second surface which, in the operative" should read "bone, and a second surface which, in the operative"

Signed and Sealed this
Nineteenth Day of April, 2022

*Katherine Kelly Vidal*

Katherine Kelly Vidal
*Director of the United States Patent and Trademark Office*